United States Patent [19]

Toja et al.

[11] 4,340,607
[45] Jul. 20, 1982

[54] ANTIMICROBIAL 3H-NAPHTHO[1,2-D]IMIDAZOLES

[75] Inventors: Emilio Toja, Milan; Amedeo Omodei-Sale, Voghera; Domenica Selva, Milan, all of Italy

[73] Assignee: Gruppo Lepetit S.p.A., Milan, Italy

[21] Appl. No.: 236,468

[22] Filed: Feb. 20, 1981

Related U.S. Application Data

[63] Continuation-in-part of Ser. No. 104,490, Dec. 17, 1979, abandoned.

[30] Foreign Application Priority Data

Dec. 21, 1978 [GB] United Kingdom ............... 49690/78

[51] Int. Cl.³ ................. A61K 31/415; C07D 235/02; C07D 405/02
[52] U.S. Cl. ............................. 424/273 B; 548/326; 564/428
[58] Field of Search ..................... 548/326; 424/273 B

[56] References Cited

FOREIGN PATENT DOCUMENTS 1137625 10/1962 Fed. Rep. of Germany .

*Primary Examiner*—Richard A. Schwartz

[57] ABSTRACT 3H-naphtho[1,2-d]imidazole derivatives of formula

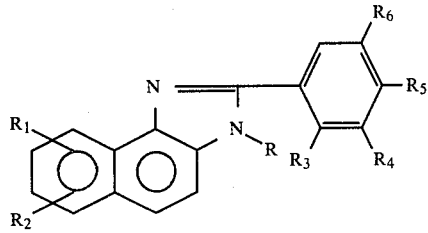

wherein R stands for $(C_{1-6})$alkyl, $(C_{3-6})$alkenyl, $(C_{3-6})$alkynyl or $(C_{3-7})$cycloalkyl, $R_1$ and $R_2$, each independently may represent hydrogen, halogen, $(C_{1-4})$alkyl, $(C_{1-4})$alkylthio, $(C_{1-4})$alkoxy or halo$(C_{1-4})$alkoxy, $R_3$ and $R_4$, each independently, represent hydrogen or $(C_{1-4})$alkoxy, $R_5$ stands for hydrogen, $(C_{1-4})$alkyl, $(C_{3-4})$alkoxy, mono- and di-$(C_{2-4})$alkylamino, $(C_{2-4})$alkanoylamino, carboxymethoxy and [carbo$(C_{1-4})$alkoxy]methoxy. and $R_6$ is hydrogen or $R_4$ and $R_6$ taken together may represent a methylenedioxy radical with the proviso that when $R_5$ is hydrogen at least one of $R_3$ and $R_4$ must be different from hydrogen, useful as antimicrobial agents.

4 Claims, No Drawings

ANTIMICROBIAL 3H-NAPHTHO[1,2-D]IMIDAZOLES

This application is a continuation-in-part of U.S. patent application Ser. No. 104,490 filed on Dec. 17, 1979, now abandoned.

The present invention relates to novel 3H-naphtho[1,2-d]imidazole derivatives of the following general formula I

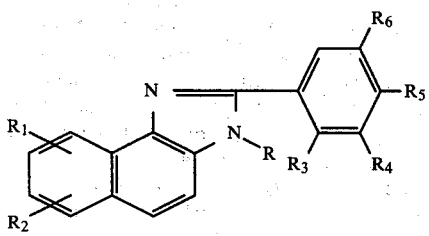

wherein R stands for $(C_1-C_6)$alkyl, $(C_3-C_6)$alkenyl, $(C_3-C_6)$alkynyl or $(C_{3-7})$cycloalkyl, $R_1$ and $R_2$, each independently may represent hydrogen, halogen, $(C_{1-4})$alkyl, $(C_{1-4})$alkylthio, $(C_{1-4})$alkoxy or halo$(C_{1-4})$alkoxy, $R_3$ and $R_4$, each independently, represent hydrogen or $(C_{1-4})$alkoxy, $R_5$ stands for hydrogen, $(C_{1-4})$alkyl, $(C_{3-4})$alkoxy, carboxy-methoxy, [carbo$(C_{1-4})$alkoxy]methoxy, mono- and di-$(C_{2-4})$alkylamino and $(C_{2-4})$alkanoylamino, and $R_6$ is hydrogen or $R_4$ and $R_6$ taken together may represent a methylenedioxy radical; with the proviso that when $R_5$ is hydrogen at least one of $R_3$ and $R_4$ must be different from hydrogen; and salts therewith of pharmaceutically acceptable acids.

The novel compounds of the present invention possess antimicrobial utility.

Naphth[1,2-d]imidazoles bearing a 2-hydroxyphenyl or a 4-dimethylaminophenyl group at the 2-position are known from German Pat. No. 1,137,625 which reports several thiazole, oxazole and imidazole derivatives with photoconductive properties, that suitably be employed for electrophotographic reproduction.

Naphth[1,2-d]imidazole bearing a nitro-substituted phenyl group at the 2-position is known from the article by F. W. Lown and M. H. Akhtor published in Can. J. Chem. 49, (1971), 1610, where the authors discuss the mechanism involved in the reaction of 1-nitroso-2-naphthylamine with 3-aroyl-aziridines.

Moreover, other naphthoimidazoles, substituted in the 2-position by an alkyl group, are described in U.S. Pat. No. 3,046,116 where it is said that these compounds can be conveniently used in the production of printing plates.

As used herein the term "$(C_{1-4})$alkyl" and the alkyl portion of other hereinlisted radicals containing a $(C_{1-4})$alkyl moiety identifies a straight or branched alkyl radical having from 1 to 4 carbon atoms such as methyl, ethyl, propyl, 1-methylethyl, butyl, 1-methylpropyl, 2-methylpropyl and 1,1-dimethylethyl while the term "$(C_{1-6})$alkyl" designates a straight or branched alkyl radical containing up to 6 carbon atoms such as those listed before, pentyl, 1-ethylpropyl, 1-methylbutyl, 1,1-dimethylpropyl, 1,2-dimethylpropyl, 2,2-dimethylpropyl, hexyl, 1-methylpentyl, 4-methylpentyl, 1,3-dimethylbutyl, 3,3-dimethylbutyl and the like. The expression "$(C_{3-6})$alkenyl" identifies straight or branched alkenyl groups containing 3 to 6 carbon atoms and one or two double bonds, such as, 2-propenyl, 1-methyl-2-propenyl, 2-butenyl, 1-methyl-2-butenyl, 2,4-hexadienyl, 1-methyl-2,4-pentadienyl and the like. The term "$(C_{3-6})$alkynyl" designates straight or branched alkynyl groups containing 3 to 6 carbon atoms and one or two triple bonds, such as, 2-propynyl, 1-methyl-2-propynyl, 2-butynyl, 1-methyl-2-butynyl, 2,4-hexadiynyl and the like. The term "$(C_{3-7})$cycloalkyl" indicates cycloalkyl radicals of 3 to 7 carbon atoms selected from cyclopropyl, cyclobutyl, cyclopentyl, cyclohexyl and cycloheptyl. The expression "$(C_{1-4})$alkoxy" identifies straight or branched alkoxy radicals having at most 4 carbon atoms which are selected from methoxy, ethoxy, propoxy, 1-methylethoxy, butoxy, 1-methylpropoxy, 2-methylpropoxy, 1,1-dimethylethoxy.

The term and the moiety "halogen" essentially identifies chloro, bromo, and fluoro.

A preferred group of compounds comprises those compounds of formula I wherein R stands for $(C_{1-6})$alkyl, $R_1$ and $R_2$ are hydrogen, $R_3$ and $R_4$ each independently, represent hydrogen or $(C_{1-4})$alkoxy, $R_5$ stands for hydrogen, $(C_{1-4})$alkyl, $(C_{3-4})$alkoxy, carboxymethoxy, [carbo$(C_{1-4})$alkoxy]methoxy, mono- and di-$(C_{2-4})$alkylamino, or $(C_{2-4})$alkanoylamino, and $R_6$ is hydrogen or $R_4$ and $R_6$ taken together may represent a methyelenedioxy radical, with the proviso that when $R_5$ is hydrogen, at least one of $R_3$ and $R_4$ must be different from hydrogen, or a non-toxic pharmaceutically acceptable acid addition salt thereof.

These addition salts are obtained by treating compounds of formula i above with pharmaceutically acceptable acids. As acids suitable for the formation of therapeutically acceptable salts there may be mentioned, for example, hydrohalide, sulfuric and phosphoric acids, nitric and perchloric acids; aliphatic, alicyclic, aromatic and heterocyclic carboxylic or sulfonic acids, such as formic, acetic, propionic, succinic, glycolic, lactic, malic, tartaric, citric, ascorbic, maleic, hydroxymaleic, pyruvic acid; phenylacetic, benzoic, para-aminobenzoic, anthranilic, para-hydroxybenzoic, salicylic, para-aminosalicylic or embonic acid, methanesulfonic, ethanesulfonic, hydroxyethanesulfonic, ethylenesulfonic acid; halobenzenesulfonic, toluenesulfonic, naphthalenesulfonic acids or sulfanilic acid.

These or other salts of the new compounds may also be used for purifying the resulting compounds by converting them into salts, isolating the latter and liberating the free compound from them. In view of the close relationship between the new compounds in the free form and in the form of their salts what has been said above and hereinafter with reference to the free compounds concerns also the corresponding salts.

A general method for preparing the novel compounds comprises the condensation between a naphthalenediamine of formula II

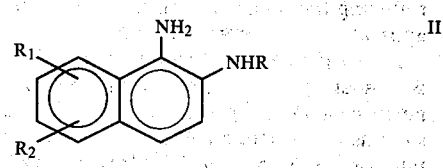

wherein R, $R_1$ and $R_2$ are as defined before, and a suitably selected aldehyde of formula

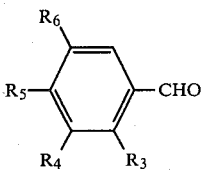

wherein $R_3$, $R_4$, $R_5$ and $R_6$ are as defined before, to yield an intermediate imidazoline which is subsequently oxidized to end product. The overall reaction is better illustrated in the following scheme A

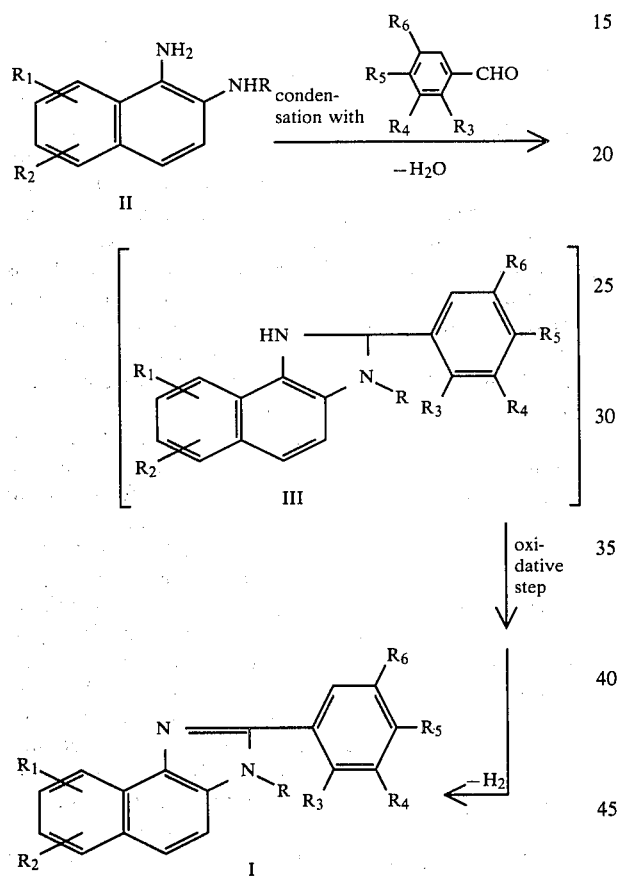

wherein the square brackets mean that the intermediate compound placed within them can be further processed without previous separation.

Widely varying conditions can be used to bring about the condensation between the naphthalenediamine and the aldehyde; however rather good results have been obtained adding an equimolecular proportion or a slight excess of the aldehyde to a solution of the compound of formula II in an inert high boiling organic solvent such as for instance xylene, toluene, or cymene and then refluxing the obtained reaction mixture in a Dean-Stark apparatus under inert atmosphere.

As for the oxidative step which in the above scheme is visualized as a simple dehydrogenation, it can be performed in the presence of a mild oxidizing agent, such as for instance manganese dioxide or cupric acetate, or better with a dehydrogenating agent suitably selected from the group of metals or metal oxides generally employed and named as "hydrogenating catalysts" such as for instance Palladium, Platinum, Ruthenium, Rhodium, Platinum dioxide, either in powder form or adsorbed on a charcoal or asbestos carrier, and Raney-Nickel. The obtained reaction products are recovered by conventional procedures which involve filtration of the hot solution and evaporation of the solvent under reduced pressure. Purification of the raw material thus obtained is achieved simply by crystallization or by means of chromatographic techniques.

The starting naphthalenediamine derivatives of formula II are generally novel and may be prepared through different routes; for instance, in J. Org. Chem. 37 (22), 3566 (1972), the synthesys of $N^2$-isopropyl-naphthalen-1,2-diamine is reported through (a) nitration of $\beta$-naphthaleneamine to 1-nitro-2-naphthaleneamine, (b) exchange of the amino group with a chlorine atom, (c) amination with isopropylamine and finally (d) reduction of the nitro group to amino.

Other methods moreover can be gathered from the literature considering the particular reactivity of the naphthalene substratum.

The process we have generally employed for preparing the starting naphthalenediamine derivatives involves the reduction of a N-substituted-1-nitroso-2-naphthaleneamine of formula

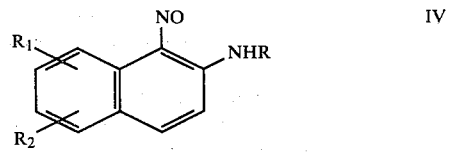

wherein R, $R_1$ and $R_2$ are as defined before, by means of hydrogen gas in the presence of a hydrogenating catalyst. Various hydrogenation catalysts can be employed to bring out the conversion to diamines and generally the same metals and metal oxides employed in the oxidative step of scheme A are preferably used, i.e. Palladium, Platinum, Ruthenium, Rhodium, Platinum dioxide, either in powder form or adsorbed on a carrier, and Raney-nickel. Also the reaction conditions may vary widely since all the catalysts listed above are active, and are preferably used, at room temperature and atmospheric pressure but can suitably be employed also up to 4 atmospheres. Solvents which can conveniently be employed in this reaction are selected from lower aliphatic alcohols such as methanol and ethanol and aromatic hydrocarbons such as for instance benzene, toluene, xylene and cymene.

Alternatively reduction of the N-substituted-1-nitroso-2-naphthalenamine derivative can also be accomplished by using as reducing agents metals such as tin, zinc or aluminum in an acidic medium according to well known procedures.

The starting nitroso compounds have been synthetized according to the method described by S. T. Morgan and F. P. Evens in J. Chem. Soc. 115, 1140 (1919), through acid-catalyzed rearrangement of a 2-(N-nitroso-N-substituted)naphthylamine or more conveniently through reaction of primary amines with 1-nitroso-2-naphthol according to E. W. Malmberg and C. S. Hamilton in J. Am. Chem. Soc. 70, 2415 (1948).

The above reported method for preparing the starting naphtalenediamines II from the corresponding N-substituted-1-nitroso-2-naphthaleneamines is of particular value for many reasons. First of all in fact the reduction reaction does not require drastic conditions but on the contrary it proceeds rapidly at room temperature and atmospheric pressure, secondly the reaction conditions themselves, the solvents and the starting nitroso-compounds employed are particularly safe from the industrial point of view; thirdly the naphthalenediamines thus obtained are not necessarily separated from the reaction mixture and the condensation with the suitably selected aldehyde can be carried out out without any working up of the reaction mixture containing the hydrogenated compound of formula II before adding the aldehyde. In this case, if separation of the naphthalenediamines is not required, also the reduction of the N-substituted-1-nitroso-2-naphthaleneamines will be carried out in an inert high-boiling organic solvent.

Moreover, since catalyzed reduction, which takes place on the catalyst's surface, is a reversible process, the same catalysts employed for reducing the nitrosonaphthaleneamines can be conveniently employed in the absence of hydrogen, in the dehydrogenation procedure. The interaction between a naphthalenediamine of formula II and an acid derivative which may be an acyl chloride, anhydride or ester provides an other convenient route to the naphthoimidazoles of the present invention. More particularly, the naphthalenediamine is contacted with a compound of formula

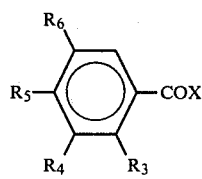

wherein $R_3, R_4, R_5$ and $R_6$ are as defined before and X may represent a chlorine atom a group $—OR_7$ wherein $R_7$ may be the same radical

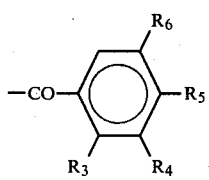

or a trifluoroacetyl, ethoxycarbonyl or alkyl sulfonyl moiety or, a group $—OR_8$ wherein $R_8$ is a methyl or ethyl radical. This two step reaction involves formation of a mono-acylated naphthalenediamine as the key intermediate according to the following scheme B:

SCHEME B

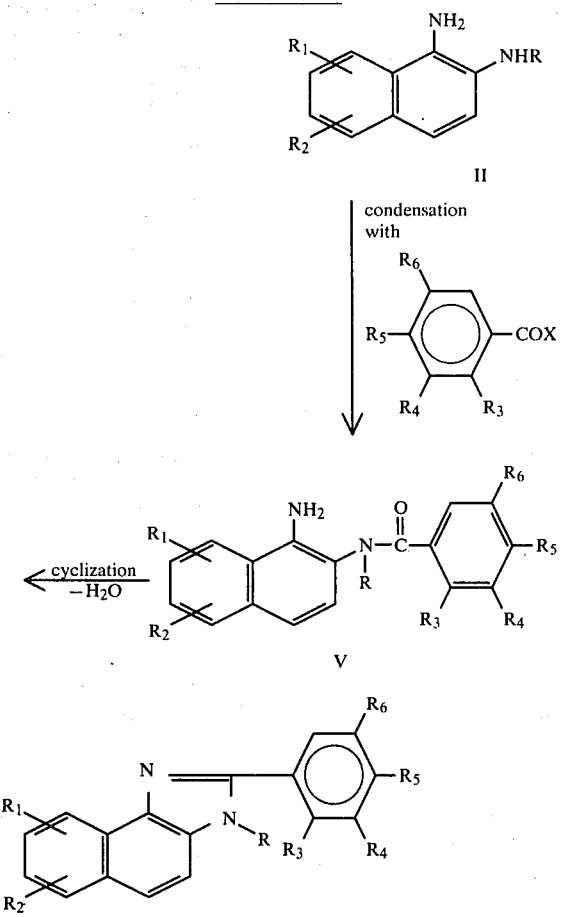

As for the first step which leads to the intermediate mono-acylated compounds, we found that high yields can be realized when an equimolecular mixture of a naphthalendiamine II and an acid derivative

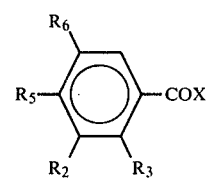

is dissolved in an anhydrous inert organic solvent selected from lower aliphatic halogenated and aromatic hydrocarbons in the presence of a tertiary organic nitrogen base which should block the inorganic or organic acid which forms during the course of the reaction.

Finally, conversion of the mono-acylated intermediate to the desired end product, through elimination of water, is carried out by refluxing it in an inert organic solvent optionally in the presence of an acidic catalyst such as sulphuric or p-toluenesulphonic acid. Recovery and purification of the end naphthoimidazoles, involves the same conventional procedures already described in the first process. Furthermore some compounds of formula I may be obtained also through chemical modifications of other compounds, corresponding to formula I, prepared according to one of the reaction schemes outlined before.

For instance, compounds wherein $R_5$ is $(C_{3-4})$alkoxy, carboxymethoxy, or [carbo$(C_{1-4})$alkoxy]methoxy are conveniently prepared by reaction of the corresponding hydroxyphenyl derivatives, prepared as described before, with suitable agents such as $(C_{3-4})$alkyl halogenides, tosylates or mesylates, an α-haloacetic acid and its $(C_{1-4})$alkyl esters. A convenient route leading to mono$(C_{2-4})$alkylaminophenyl compounds in high yields, consists of preparing the sodium derivative of the amidic nitrogen atom of a corresponding acylamino derivative, then substituting it by means of an alkylating agent and finally splitting of the protecting acyl group by alkaline hydrolysis.

It is intended that alternative methods which can suitably be employed for transforming a pre-existing radical into another falling within the given meanings, although not spefically disclosed, are to be considered within the scope of the invention.

The compounds of the present invention show an appreciable antimicrobial effect mainly against fungi such as various Trichophyton species, for instance *Trychophyton mentagrophytes, Trychophyton Schoenleinii* and *Trichophyton versicolor.*

More particularly, concentrations varying from about 3 to about 25 γ/ml of the compounds of Examples 1, 2, 3, 4, 5, 7, and 8 inhibit the growth of these microorganisms in vitro.

The use of the novel compounds as antimicrobial agents, which is a further specific object of the present invention refers to all industrially applicable aspects and acts of said use including the embodying of the novel compounds or their salts into pharmaceutical compositions.

For antimicrobial use the compounds of the invention are compounded into topical preparations such as ointments, creams, powders and the like in concentration of from 0.1 to 10% to be applied one or more times a day as required. Ointments and creams are prepared by incorporating the active ingredient into an ointment base such as for instance a oleaginous base prepared from vegetable and animal fats, a hydrocarbon base prepared from petrolatum and wax or, preferably a polyethylenglycol ointment base. Powders are prepared by mixing the active ingredient in the form of a very finely subdivided powder with a chemically inert vehicle as known in the art.

The following examples illustrate the process of the invention and describe in detail some compounds of general formula I without limiting the scope of the invention.

EXAMPLE 1

2-(3-methoxyphenyl)-3-methyl-3H-naphtho[1,2-d]imidazole 13.75 g of 3-methoxy benzoyl chloride (0.08 mole) dissolved in 50 cc of methylene chloride is added to a solution of 14.60 g of $N^2$-methylnaphthalene-1,2-diamine (0.084 mole) and 11.3 cc of triethylamine (0.08 mole) in 100 cc of methylene chloride, and the obtained reaction mixture is allowed to stand at room temperature for about one hour. Then it is heated to the reflux temperature for 16 hours, cooled to room temperature and filtered over bleaching earth. The filtrate is diluted with 200 cc of methylene chloride, washed twice with water, once with 5% sodium bicarbonate and then with water up to neutral reaction of the aqueous phase. The methylene chloride solution, dried over sodium sulphate, is concentrated to dryness yielding a residue which taken up with 300 cc of benzene is then poured into a 500 cc flask equipped with a Dean Stark apparatus. 0.18 g of p-toluensulphonic acid is gradually added to this solution heated to the reflux temperature.

After 4 hours, the reaction mixture is cooled to room temperature and filtered. The filtrate washed with water, is dried over sodium sulphate and then concentrated to dryness yielding 12.57 g of the compound of the title. M.p. 148°–49° C. (from ethanol).

EXAMPLE 2

3-methyl-2-[4-(1-methylethoxy)phenyl]-3H-naphtho[1,2-d]imidazole

A solution of 11.16 g (0.06 mole) of 2-methylamino-1-nitrosonaphthalene in 800 cc of toluene is hydrogenated at room temperature and at the atmospheric pressure in the presence of 3 g of Palladium-on-carbon. After one hour, when the theoretical amount of hydrogen has been consumed, 0.06 mole of 4-(1-methylethoxy)-benzaldehyde are added and the obtained reaction mixture is heated to the reflux temperature under an inert atmosphere for about 3 hours. The water which forms during the reaction distillates as binary azeotrope with toluene and is separated through a Dean-Stark apparatus. Then further 1.5 g of 5% Palladium-on-carbon are added and reflux is prolonged for two additional hours. Filtration of the hot solution followed by concentration of the filtrate to dryness under vacuum affords a residue which has been purified by cristallization from ethyl ether. M.p. 144°–5° C.

EXAMPLES 3 TO 7

The following compounds are prepared by operating according to the procedures of the foregoing example, by hydrogenating the starting N-methyl-1-nitrosonaphthalenamine, condensing the obtained diamino compound with a suitable selected aldehyde and then dehydrogenating the resulting imidazoline derivative.

(3) 3-methyl-2-(4-methylphenyl)-3H-naphtho[1,2-d]imidazole. M.p. 135°–6° C. (from diisopropyl ether)

(4) N,N-diethyl-4-(3-methyl-3H-naphtho[1,2-d]imidazol-2-yl)benzenamine. M.p. 161°–162.5° C. (from ethyl acetate)

(5) 2-(1,3-benzodioxol-5-yl)-3-methyl-3H-naphtho[1,2-d]imidazole. M.p. 200°–201° C. (from acetone)

(6) N-[4-(3-methyl-3H-naphtho[1,2-d]imidazol-2-yl)phenyl]acetamide. M.p. 271°–72° C. (from ethanol).

(7) 2-(2-methoxyphenyl)-3-methyl-3H-naphth[1,2-d]imidazole M.p. 132°–33° C.

EXAMPLE 8

[4-(3-methyl-3H-naphtho[1,2-d]imidazol-2-)phenoxy]acetic acid ethyl ester.

60 cc (0.06 mole) of 1 N NaOH are dripped, over a period of time of two hours, into a vigorously stirred solution of 8.22 g (0.03 mole) of 4-(3-methyl-3H-naphth[1,2-d]imidazol-2-yl)phenol (prepared by following the procedure of example 2 but using 4-hydroxy benzaldehyde instead of 4-ethoxybenzaldehyde), 0.35 g (0.03 mole) of benzyl-tributyl ammonium chloride, and 10.4 cc (0.09 mole) of bromoacetic acid ethyl ester in 300 cc of methylene chloride. The reaction mixture is stirred for further two hours. Then 10.4 cc of bromoacetic acid ethyl ester and 60 cc on 1N NaOH are added over a period of two hours still under stirring. Stirring is prolonged for further two hours and the addition of bromoacetic acid ethyl ester and NaOH is repeated under the same conditions.

Upon filtration the unreacted starting material is recovered from the solid and purified by crystallization from dimethylformamide (3.95 g) while from the filtrate the organic layer is separated, washed with water and dried over MgSO₄. The solvent is then evaporated and the residue is dissolved in 50 cc or isopropanol and diluted with diethyl ether to precipitate the catalyst employed in the reaction which is filtered off. Evaporation of the solvent affords 8.6 g of a raw product which is purified by column chromatography using cyclohexane containing increasing amounts of ethyl acetate up to 8:2 as the eluting system; yield 45%. M.p. 103°–4° C. (from isopropanol).

EXAMPLE 9

[4-(3-methyl-3H-naphth[1,2-d]imidazol-2-yl)phenoxy]acetic acid 3.99 g (0.011 mole) of the compound of the foregoing example, 20 cc of 10% NaOH, and 40 cc of methanol are heated at the reflux temperature for about 30 minutes. Then the methanol is boiled off, the mixture is cooled to 5° C. and the pH is brought to 5 by the addition of glacial acetic acid. The solid which precipitates is recovered by filtration and crystallized from ethanol. Yield 53%. M.p. 227° C.

By operating according to the procedures of the foregoing examples the following compounds may be prepared:

3-ethyl-2-(3-methoxyphenyl)-3H-naphtho[1,2-d]imidazole 3-methyl-2-[4-(1-methylethyl)phenyl]-3H-naphtho[1,2-d]imidazole N,N-di(1-methylethyl)-4-(3-methyl-3H-naphtho[1,2-d]imidazol-2-yl)benzenamine N-[4-(3-methyl-3H-naphtho[1,2-d]imidazol-2-yl)phenyl]propionamide N-[4-(3-ethyl-3H-naphtho[1,2-d]imidazol-2-yl)phenyl]acetamide 7-methoxy-2-(2-methoxyphenyl)-3-methyl-3H-naphtho[1,2-d]imidazole 2-(4-carboxy-methoxyphenyl)-7-methoxy-3-methyl-3H-naphtho[1,2-d]imidazole

We claim:

1. 3H-naphtho[1,2-d]imidazole derivative having the following formula

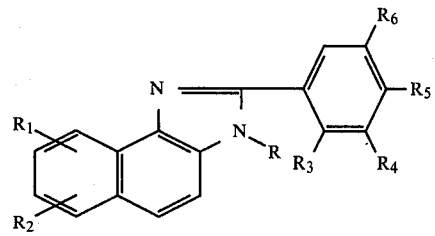

wherein R stands for $(C_{1-6})$alkyl, $(C_{3-6})$alkenyl, $(C_{3-6})$alkynyl or $(C_{3-7})$cycloalkyl, $R_1$ and $R_2$ each independently may represent hydrogen, halogen, $(C_{1-4})$alkyl, $(C_{1-4})$alkylthio, $(C_{1-4})$alkoxy or halo$(C_{1-4})$alkoxy, $R_3$ and $R_4$, each independently represents hydrogen or $(C_{1-4})$alkoxy, $R_5$ stands for hydrogen, $(C_{1-4})$alkyl, $(C_{3-4})$alkoxy, carboxymethoxy, [carbo$(C_{1-4})$alkoxy]methoxy or $(C_{2-4})$alkanoylamino and $R_6$ is hydrogen or $R_4$ and $R_6$ taken together may represent a methylenedioxy radical, with the proviso that when $R_5$ is hydrogen at least one of $R_3$ and $R_4$ must be different from hydrogen; or a non-toxic pharmaceutically acceptable acid addition salt thereof.

2. A compound as in claim 1 wherein R stands for $(C_{1-6})$alkyl, $R_1$ and $R_2$ are hydrogen, $R_3$ and $R_4$, each independently, represent hydrogen or $(C_{1-4})$alkoxy, $R_5$ stands for hydrogen, $(C_{1-4})$alkyl, $(C_{3-4})$alkoxy, carboxymethoxy, [carbo$(C_{1-4})$alkoxy]methoxy or $(C_{2-4})$alkanoylamino, and $R_6$ is hydrogen or $R_4$ and $R_6$ taken together may represent a methylenedioxy radical, with the proviso that when $R_5$ is hydrogen, at least one of $R_3$ and $R_4$ must be different from hydrogen; or a non-toxic pharmaceutically acceptable acid addition salt thereof.

3. An antimicrobial composition which comprises from about 0.1 percent by weight to about 10 percent by weight of a compound of formula I

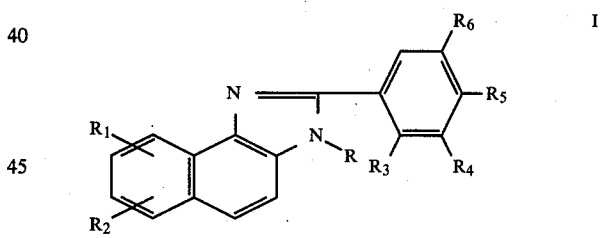

wherein R, $R_1$, $R_2$, $R_3$, $R_4$, $R_5$, and $R_6$ are as defined in claim 1, or a salt therewith of a pharmaceutically acceptable acid in admixture with a topical pharmaceutical carrier.

4. A method for combatting microbial infections in animals which comprises topically applying to the mucous membranes or to the skin of an animal in need thereof an effective amount of a composition of claim 3 one or more times a day.

* * * * *